United States Patent [19]

Milani

[11] Patent Number: 4,800,894

[45] Date of Patent: Jan. 31, 1989

[54] PROTECTION OF EKG MONITOR AGAINST ELECTRICAL SURGICAL INTERFERENCE

[75] Inventor: Dean L. Milani, Highland Park, Ill.

[73] Assignee: Medical Research Laboratories, Niles, Ill.

[21] Appl. No.: 928,807

[22] Filed: Nov. 7, 1986

[51] Int. Cl.[4] .................................................. A61B 5/00
[52] U.S. Cl. .................................. 128/419 R; 128/908; 128/303.13
[58] Field of Search .................... 128/419 D, 695, 696, 128/709, 710, 908, 419 R, 303.13, 303.14, 303.15, 303.17

[56] References Cited

U.S. PATENT DOCUMENTS

| | | | |
|---|---|---|---|
| 3,895,635 | 7/1975 | Justus et al. | 128/303.13 |
| 3,960,141 | 6/1976 | Bolduc | 128/303.13 |
| 4,106,494 | 8/1978 | McEachern | 128/696 |
| 4,109,223 | 8/1978 | Tenkman et al. | 128/303.13 |
| 4,164,215 | 8/1979 | Finlayson et al. | 128/696 |
| 4,245,649 | 1/1981 | Schmidt-Andersen | 128/696 |
| 4,331,157 | 5/1982 | Keller, Jr. et al. | 128/419 R |
| 4,331,158 | 5/1982 | Partridge | 128/709 |
| 4,378,021 | 3/1983 | Strand | 128/709 |
| 4,517,976 | 5/1985 | Murakoshi et al. | 128/303.15 |
| 4,577,639 | 3/1986 | Simon et al. | 128/709 |

Primary Examiner—Francis J. Jaworski
Assistant Examiner—Timothy J. Keegan
Attorney, Agent, or Firm—Trexler, Bushnell, Giangiorgi & Blackstone, Ltd.

[57] ABSTRACT

A protective device for an EKG monitor for use in surgical electrocautery which employs an electrocautery surgical knife supplied with radio frequency power and an EKG monitoring apparatus having an input and including a scope providing an EKG display. Electrodes are provided for attachment to a surgical patient and are connected to the apparatus by the protective device, which includes a radio frequency detector and disabling apparatus which removes signal from the EKG monitor input in the presence of radio frequency energy.

3 Claims, 1 Drawing Sheet

PROTECTION OF EKG MONITOR AGAINST ELECTRICAL SURGICAL INTERFERENCE

BACKGROUND OF THE INVENTION

It is practically universal practice to monitor the pulse and respiration of a patient anesthetized for surgery. An EKG (electrocardiogram) is continuously displayed on a monitor. Thus, the anesthesiologist and/or surgeon can at all times ascertain the status of the patient's cardiovascular activity. A grounding electrode or "pad" is provided beneath the patient, commonly beneath the buttocks in the supine patient. Additional "pickup" electrodes are applied to the patient's body, commonly on the chest. All of the electrodes are connected to a commercially-available EKG monitor for displaying the pattern of electrical impulses detected as a result of cardiac activity on a cathode ray screen or other visual display device.

In certain types of surgery it is common to apply electrocautery in which a surgical knife is supplied with a relatively high level of radio frequency energy so that blood vessels or other tissue are cauterized and sealed immediately upon cutting. However the presence of such radio frequency signal or energy on the patient's body and particularly in the region of the EKG "pickup" electrodes causes severe interference with the operation of the EKG monitor and resultant electrocardiogram. In fact such radio frequency interference has been known to render the monitor totally inoperable for many seconds, resulting in a loss of the desired continuous observation of cardiovascular activity as reflected by the EKG display.

If electrocautery is practiced with no precautions, the radio frequency signal will force the EKG readings completely "off scale", and will overload the EKG circuits to the point where it may be many seconds before the monitor can recover after the radio frequency energy is turned off. Some effort has been made to correct this situation using an electrical surgical interference supression (ESIS) filter between the electrodes and the monitor. Even with such a filter something on the order of 30% of the radio frequency gets through to the monitor screen. This produces a distorted image on the best of monitors, and sends others completely off scale. Recovery time is somewhat improved due to the diminished radio frequency signal, but still requires several seconds in most cases.

OBJECTS AND SUMMARY OF THE INVENTION

It is a general object of the present invention to provide a novel protective device which prevents radio frequency interference at the input to an EKG monitor even in the presence of a relatively strong radio frequency signal.

In attaining the foregoing object, I provide an EKG monitor oscilloscope with a "time out" circuit which simply grounds the input to the monitor scope in the presence of a radio frequency signal. The monitor circuits thus are not overloaded. A zero or baseline signal is provided on the monitor's scope so that all concerned may see that there is a radio frequency signal present. Upon cessation of the radio frequency signal, the monitor immediately responds to the EKG signal and the scope instantaneously displays the EKG without the necessity of any waiting for overloaded circuits to recover.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in the several figures of which like reference numerals identify like elements, and in which:

DETAILED DESCRIPTION OF THE ILLUSTRATED EMBODIMENT

Figure 1:
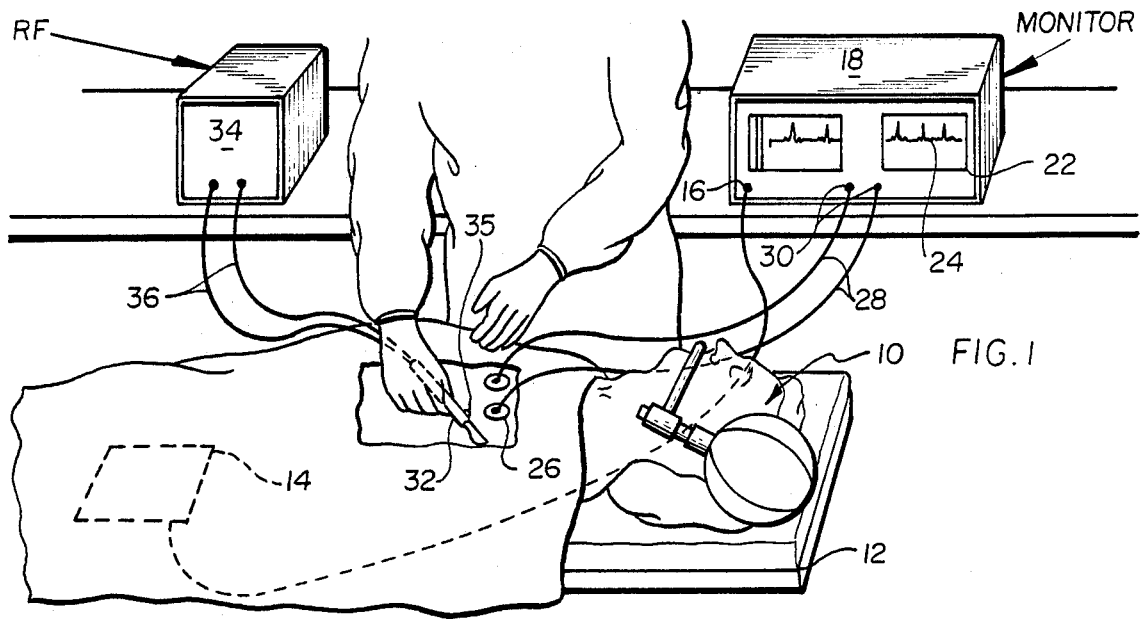
FIG. 1 is a somewhat diagrammatic view illustrating an EKG monitor and electrocautery apparatus in a surgical setting in which the invention may be advantageously used.

Turning now in greater detail to the drawings, and first to FIG. 1, there is shown somewhat diagrammatically a patient 10 lying supine on an operating table 12. A grounding electrode 14 is positioned below the patient's body, specifically under the buttocks, and is connected to an input terminal 16 of a monitor 18 by means of a flexible electrically conductive cable or wire 20. The monitor includes standard EKG electronic circuitry and a scope or display device (e.g., a cathode ray tube) 22 for displaying an electrocardiogram trace 24. Two additional "pickup" electrodes 26 are placed on or adjacent the patient's chest and are connected by further wires 28 to further input terminals 30 of the monitor.

There is also shown somewhat diagrammatically an electrocautery knife 32 operated by radio frequency energy from a radio frequency generator 34 by means of a pair of wires 36, which may be a shielded cable. When the radio frequency generator 34 is turned on as by means of a button 35 or the like on the knife 32, radio frequency energy is emitted by the knife 32. This radio frequency energy is unfortunately picked up by the electrodes 26 when the energized knife is in contact with the patient during a surgical procedure. The result is that the circuits of the monitor are saturated, and the display on the scope is driven off scale. When the knife is removed or the radio frequency energy is shut off, it can be expected that at least several seconds will be required for the monitor circuits to recover before a useable display can be provided again on the scope 22.

Figure 2:
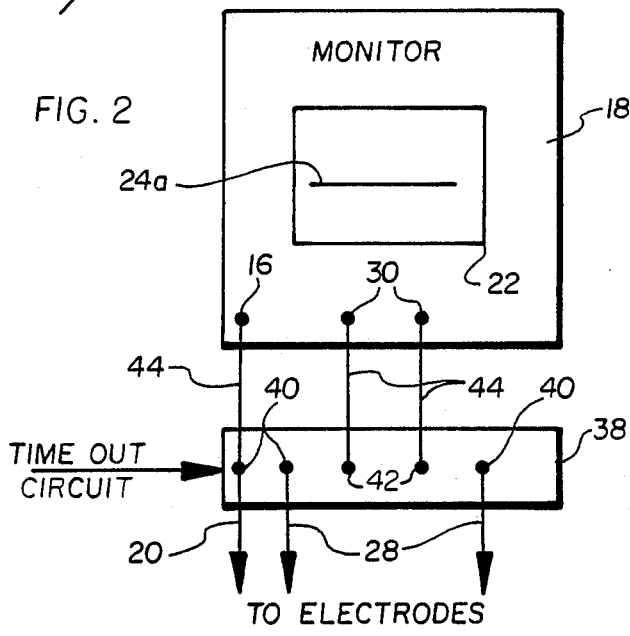
FIG. 2 is a block diagram illustrating the invention in connection with a relevant portion of the apparatus of FIG. 1.

Turning now to FIG. 2, certain of the parts of FIG. 1 are again illustrated in connection with the invention. The protective device of the invention, which I have also termed "time out circuit" 38 is interposed between the electrodes 14, 26 and the monitor 18. Specifically, the "time out" circuit is provided with input terminals 40 to which the electrode wires 20 and 28 are connected, and output terminals 42 which are connected by wires 44 to the input terminals 16 and 30 of the monitor 18. The design and operation of the "time out" circuit 38 are such that when radio frequency energy is transmitted on the wires 20, 28, a true electrical ground is applied to the terminals 16, 30 through the wires 44, whereby the monitor scope 22 displays a flat "zero" or base line 24a.

Figure 4:
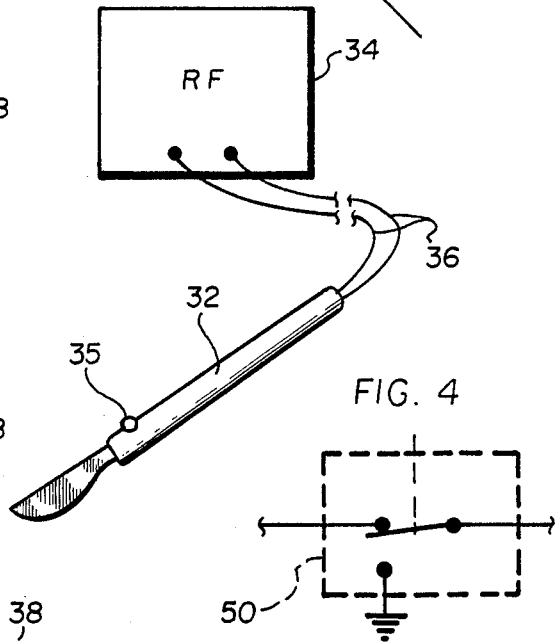
FIG. 4 is a diagram of an exemplary disabling or switching means portion of the invention.
Figure 3:
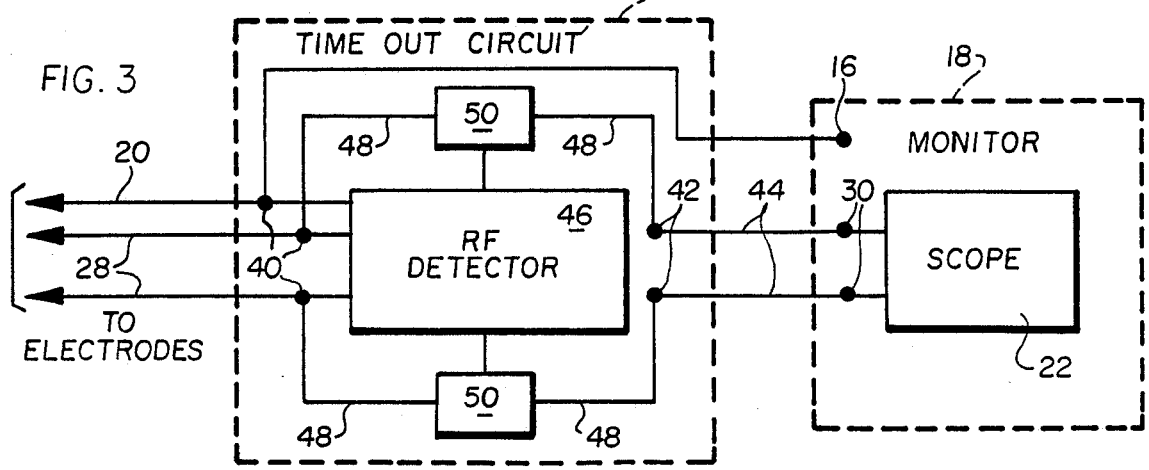
FIG. 3 is a block diagram illustrating further details of the invention.

More particularly, and as shown in FIGS. 3 and 4, the "time out" circuit 38 includes a radio frequency detector 46. Wires 48 extend around the radio frequency detector from the input electrodes 40 to the output electrodes 42. Disabling or switching means 50 are interposed in the wires 48. These switching means 50 are "normally closed" so that in the absence of any radio frequency energy on wire 28 the EKG signal will be passed through to the monitor 18 for the normal display as in FIG. 1. However, when radio frequency energy is detected by the radio frequency detector 46, the radio frequency detector applies a control signal to both of the switching means 50. The disabling or switching means respond by changing state so as to apply ground to wires 48 and to the input terminals 30 of the monitor. The flat line display 24a o FIG. 2 is produced in response to this grounding of terminals 30.

Since the input to the monitor in general is at a ground or zero level when RF energy is present, there is no possible overloading of circuits, and hence there is no recovery time needed. The radio frequency used in electrocautery lies within a relatively well-defined narrow band, and accordingly, the radio frequency detector 46 is selected specifically to detect signal frequencies within this band.

In accordance with the present invention, an electrocardiogram trace is normally displayed on a monitor scope for an anesthesized surgical patient. Whenever a radio frequency signal from an electrocautery knife is picked up by the EKG electrodes, the "time out" circuit instantly grounds the input to the monitor, whereby the scope produces a baseline or zero straight line display. Circuits are therefore not overloaded, and there is thus no possible damage to the monitor circuits. Furthermore, the instant radio frequency energy is shut off or the knife removed, the normal EKG display will resume.

While it is also possible to merely activate switching means 50 out of the normally closed condition, thus allowing monitor inputs 16, 30 to "float", we prefer to ground these inputs as described above. Such grounding causes the characteristic "baseline" display to let the operator or physician know that the protective device is operating, rather than some random "noise" display which could indicate an open circuit, a loose electrode or some other malfunction.

Moreover, the switching means 50 will be understood to be diagrammatically indicated. That is, any of a variety of devices, such as relays, solid state switching devices and the like may be utilized without departing from the invention.

While particular embodiments of the invention have been shown and described, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A protective device for EKG monitor for in surgical electrocautery and comprising an EKG monitoring apparatus having monitoring electrode input means and display means for providing a continuous instantaneous EKG display, electrodes for attachment to a surgical patient, conductive means interconnecting said electrodes and said input means of said EKG monitoring apparatus, and wherein said surgical electrocautery is carried out with an electrocautery surgical knife and a radio frequency energy source operatively connected thereto; wherein said protective device comprises electrical disabling means coupled with said input means for removing said electrodes from operative circuit connection with said input means in response to a control signal and radio frequency detector means operatively coupled with the patient and responsive to the presence of radio frequency energy for producing said control signal.

2. The device as set forth in claim 1 wherein said radio frequency detector means is coupled in circuit between said conductive means and said input means.

3. The device as set forth in claim 2 wherein said disabling means provides a grounded input to said EKG apparatus input means in response to said control signal.

* * * * *